United States Patent [19]
Hamajima et al.

[11] Patent Number: 5,629,069
[45] Date of Patent: May 13, 1997

[54] ABSORBENT PAPER AND ABSORBENT ARTICLE PROVIDED THEREWITH

[75] Inventors: Mitsugu Hamajima; Minoru Nakanishi, both of Tochigi, Japan

[73] Assignee: Kao Corporation, Tokyo, Japan

[21] Appl. No.: 561,441

[22] Filed: Nov. 21, 1995

Related U.S. Application Data

[62] Division of Ser. No. 221,777, Apr. 1, 1994, Pat. No. 5,496,626.

[30] Foreign Application Priority Data

Apr. 1, 1993 [JP] Japan .................................. 5-75690

[51] Int. Cl.$^6$ ........................................ D06N 7/04
[52] U.S. Cl. ............... 428/154; 162/112; 162/129; 162/130; 428/152; 428/397; 442/335; 442/344; 442/346; 442/389
[58] Field of Search ....................... 162/112, 129, 162/130; 428/284, 297, 298, 397, 152, 153, 154

[56] References Cited

U.S. PATENT DOCUMENTS

| | | | |
|---|---|---|---|
| 4,100,017 | 7/1978 | Flautt | 428/154 |
| 4,913,773 | 4/1990 | Knudsen et al. | 162/129 |
| 4,978,565 | 12/1990 | Pigneul et al. | 162/112 |
| 5,102,501 | 4/1992 | Eber et al. | 162/112 |
| 5,164,045 | 11/1992 | Awofeso et al. | 162/101 |

FOREIGN PATENT DOCUMENTS

| | | |
|---|---|---|
| A0278601 | 8/1988 | European Pat. Off. |
| A1600269 | 8/1970 | France. |

*Primary Examiner*—James J. Bell
*Attorney, Agent, or Firm*—Sughrue, Mion, Zinn, Macpeak & Seas

[57] ABSTRACT

An absorbent paper comprising a base layer, which is obtained by paper-sheeting a material containing a highly bulky cellulose fiber, and a surface layer being located on the base layer, which is obtained by paper-sheeting a material containing a highly bulky cellulose fiber, is disclosed. Further, an absorbent article wherein the absorbent paper is used as an absorbent is also disclosed.

7 Claims, 3 Drawing Sheets

ABSORBENT PAPER AND ABSORBENT ARTICLE PROVIDED THEREWITH

This is a divisional of application Ser. No. 08/221,777 filed Apr. 1, 1994 now U.S. Pat. No. 5,496,626.

FIELD OF THE INVENTION

This invention relates to an absorbent paper and an absorbent article provided with the same. More particularly, it relates to an absorbent paper which is excellent in liquid absorption/permeation characteristics and liquid diffusion characteristics and a thin absorbent article wherein the absorbent paper is employed as an absorbent.

BACKGROUND OF THE INVENTION

There have been proposed a number of techniques aiming at elevating the capacity of absorbing bodily fluid of paper diapers, sanitary napkins and incontinence pads and thus these products have been improved thereby. Most of these improvements include increase in absorption rate, prevention of the back-flow of the bodily fluid from the surface of an absorbent, prevention of leakage and relief of stickiness to the skin.

Regarding a material for an absorbent article, for example, it has been proposed to elevate the absorption capacity and to prevent the post-absorption back-flow by using a high-absorbent polymer, whereby a liquid is absorbed and retained by taking advantage of a physico-chemical action, i.e., ion osmotic pressure, as a substitute for hydrophilic absorbent papers or pulps whereby a liquid is absorbed through a physical microspace. In fact, this proposal contributes to the improvement in the absorption capacity. Thus absorbents comprising a combination of a pulp and a high-absorbent polymer are employed in almost all absorbent articles at present.

However, these absorbent articles are still insufficient in the prevention of leakage, i.e., the major dissatisfaction with absorbent articles resides in leakage. Also, it is pointed out that conventional absorbent articles have only a limited rate of absorbing bodily fluids and it is therefore unavoidable to use a high-absorbent polymer together with, for example, pulp having a high absorption rate, which also proves the above-mentioned disadvantage.

As one of the reasons for the unsatisfactory effect of preventing leakage of conventional absorbent articles, it may be mentioned that when pulp forms a flexible fluff absorbent layer as an absorbent, it absorbs blood on the spot and thus exhibits only poor liquid diffusion characteristics for utilizing the whole absorbent efficiently. Although the fluff pulp shows a recovery from compression and bending at a certain level in a dry state, it suffers from a serious decrease in strength in a wet state and thus scarcely shows any recovery. When stress is applied to wet pulp, therefore, the pulp undergoes compressive deformation (hereinafter referred to as "twisting"), which considerably reduces the absorption space thereof. When the absorbed bodily fluid is returned due to the twisting, the decrease in the pulp fiber space accompanying the twisting causes an increase in the transfer resistance of the bodily fluid toward the polymer. As a result, the absorption efficiency of the polymer is lowered and the re-absorption rate of the twisted absorbent as whole is also seriously lowered, which often results in leakage.

As a technique for improving the liquid diffusion characteristics of the fluff pulp, there has been reported it is possible to produce a high-density pulp by compression to give thereby improved diffusion characteristics. However, this technique not only fails to fundamentally solve the problem of twisting of pulp but also worsens the absorption efficiency of the polymer, since the inter-fiber distance of the pulp is shortened and thus the transfer resistance of bodily fluid toward the polymer is significantly elevated. Thus, conventional absorbents comprising fluff pulp are still insufficient in absorption capacity and prevention of leakage and cannot provide both a high absorption rate and good liquid diffusion characteristics at the same time.

Most of the conventional absorbent papers are those obtained by paper-sheeting natural pulp by the wet method. When a common absorbent paper obtained by sheeting natural pulp is dehydrated and dried in the dehydration/wet-pressing/drying steps during the paper-sheeting process, a strong restraint force occurs due to the interfacial tension of water and hydrogen bonds between fibers upon dehydration/drying. This restraint force makes the inter-fiber distance of the pulp very tight. As a result, the absorbent paper obtained from this pulp exhibits only a very slow absorption/permeation of a liquid. Furthermore, the pulp fiber space, by which the liquid is substantially absorbed, is extremely reduced.

Attempts have been made to elevate the bulkiness of absorbent paper by, for example, creping or embossing. However, these processing techniques can scarcely enlarge the absorption space essentially consisting of pulp fibers but only elevate the apparent thickness and thus the liquid absorption/permeation characteristics cannot be improved thereby. It has also been attempted to produce a high-bulkiness absorbent pulp by bulkily laminating pulp sheets by a dry method such as air-laying and binding these sheets together with the use of an appropriate binding agent. According to this method, an absorbent sheet, which has an extremely low density, a loose inter-fiber structure and a large absorption space in a dry state, can be obtained. When this absorbent paper absorbs a liquid, however, it shows very poor liquid diffusion characteristics in spite of its large absorption space. In addition, this sheet suffers from the same disadvantage as that of the fluff pulp, namely, it undergoes twisting/settling, when pressure is applied to it in a wet state.

There have also been used cellulose-based nonwoven fabric absorbent sheets such as rayon spun bonded sheets. In a nonwoven fabric absorbent sheet composed of a single fiber, the liquid diffusion characteristics and the liquid absorption/permeation characteristics are mutually contradictory. The liquid diffusion characteristics have a tendency to be improved by reducing the fiber diameter. In this case, however, the inter-fiber distance is shortened and thus the liquid absorption/permeation characteristics are worsened. When the fiber diameter is enlarged, on the contrary, the liquid absorption/permeation characteristics are improved but the liquid diffusion characteristics are worsened. That is to say, the liquid absorption/permeation characteristics and liquid diffusion characteristics are contradictory to each other and it was therefore impossible to obtain an absorbent sheet satisfying both of these requirements, namely, high liquid diffusion characteristics and excellent liquid absorption/permeation characteristics.

JP-A-4-89053 has reported a prior technique for obtaining a super-thin absorbent article free from leakage (the term "JP-A" as used herein means an "unexamined published Japanese patent application"). According to this patent, a super-thin absorbent article can be obtained by constructing an absorbent with the use of a combination of various absorbent sheets differing in absorption/permeation characteristics and diffusion characteristics from each other with high-absorbent polymers. However, this super-thin absorbent article has a disadvantage such that it is designed by taking the flow of bodily fluid in the absorbent article and the functions (temporary absorption/permeation/diffusion/retention of the bodily fluid) of each absorbent sheet into consideration and, as a result, the number of the absorbent sheets is increased and the structure of the absorbent becomes complicated. This disadvantage brings about undesirable results, namely, a decrease in productivity and an increase in production cost.

Accordingly, it is an object of the present invention to obtain an absorbent paper with a good performance, which has a large absorption space, good absorption/permeation characteristics and excellent diffusion characteristics, and to provide an absorbent article provided with an absorbent paper, which has an extremely high absorption capacity, suffers from little leakage, has a high thinness and can be comfortably fitted.

SUMMARY OF THE INVENTION

The present inventors have conducted extensive studies and consequently found that the above-mentioned object can be achieved by partitioning an absorbent paper into a surface layer and a base layer and appropriately blending a highly bulky cellulose fiber into these layers.

The present invention, which has been achieved on the basis of the above finding, provides an absorbent paper comprising at least one base layer, which is obtained by paper-sheeting a material containing a highly bulky cellulose fiber, and a surface layer, which is located on the base layer(s) and obtained by paper-sheeting a material containing a high-bulkiness cellulose fiber.

The present invention further provides an absorbent article having a liquid-permeable surface material, a liquid-retaining absorbent and a liquid-impermeable leakproof material wherein the above-mentioned absorbent paper and a high-absorbent polymer are employed in the absorbent.

BRIEF DESCRIPTION OF THE DRAWINGS

In FIGS. 1 to 8, each reference numeral has the following meaning:

Figure 1:
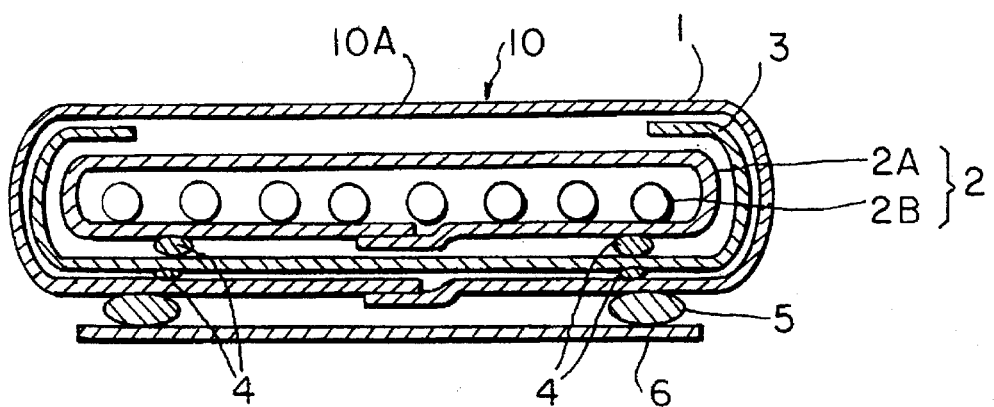
FIG. 1 is a sectional view of an absorbent article according to the Example.

1: surface material,
2: absorbent,
2A: absorbent paper,
2B: high-absorbent polymer,
3: leakproof material,
4: adhesive,
5: fixing tape,
6: peelable paper,
10: absorbent article (sanitary napkin).

DETAILED DESCRIPTION OF THE INVENTION

The absorbent paper according to the present invention comprising at least one base layer and a surface layer located on the base layers optionally has one or more appropriate intermediate layers located between the base layers and the surface layer, if necessary. The surface layer, the base layer(s) and the intermediate layer(s) are obtained by paper-sheeting a material containing a highly bulky cellulose fiber.

In the absorbent paper of the present invention, a liquid first comes in contact with the surface layer wherein the liquid is quickly absorbed and quickly penetrates to the back face, while the liquid is quickly diffused in the base layer(s). Thus an ideal sequence of liquid flow can be established.

The highly bulky cellulose fiber is rich in bulkiness and has excellent absorption/permeation characteristics. Further, it is free from an excess inter-fiber restraint force due to hydrogen bond during the dehydration/drying step, different from the wet-sheeting process of the conventional pulp, and thus the inter-fiber distance of the highly bulky cellulose fiber is not excessively tight. By blending an appropriate amount of the highly bulky cellulose fiber into the surface layer and the base layer and controlling the inter-fiber restraint force during the wet-sheeting process, a bulky absorption space is formed in each layer and both good absorption/permeation characteristics and good absorption/diffusion characteristics, which are contradictory to each other, can be achieved and sustained. That is to say, an idealized fiber space structure of the absorbent paper as the whole can be thus designed.

Examples of the highly bulky cellulose fiber include the following ones.

(a) Cellulose fibers having a stereoscopic fiber structure (twisted structure, crimped structure, folded structure and/or branched structure). Preferred examples include crosslinked fibers, wherein cellulose fibers and molecules are crosslinked to each other with the use of an appropriate crosslinking agent so as to maintain a bulky structure even in a wet state, and more preferred examples include crosslinked cellulose fibers having an improved wet modulus.

(b) Cellulose fibers having a fiber cross section area (W) of from $3.0 \times 10^{-6}$ $cm^{-2}$ to $20 \times 10^{-6}$ $cm^{-2}$, in particular, from $5.0 \times 10^{-6}$ $cm^2$ to $20 \times 10^{-6}$ $cm^2$. Preferable examples include those having a fiber cross section area (W) of from $3.0 \times 10^{-6}$ $cm^{-2}$ to $20 \times 10^{-6}$ $cm^{-2}$ and a deviation from circular form (O) of the fiber section of from 0.5 to 1.

When a cellulose fiber having a fiber cross section area (W) of less than $3.0 \times 10^{-6}$ $cm^{-2}$ is used, it is difficult to control the formation of hydrogen bonds between fibers during the paper-sheeting process. Because of this, the resulting absorbent paper tends to lower in bulkiness and liquid permeation characteristics. On the other hand, when a cellulose fiber having a fiber cross section area (W) exceeding $20 \times 10^{-6}$ $cm^{-2}$ is used, the arrangement of fibers during paper-sheeting process is highly disarranged. As a result, the resulting absorbent paper tends to lower in its liquid diffusion characteristic and tensile strength.

Alternatively, when a cellulose fiber having a deviation from circular form (O) of the fiber section of less than 0.5 is used, it becomes difficult to control the formation of hydrogen bonds between fibers due to the flatness of the fiber. As a result, the resulting absorbent sheet tends to lower in its bulkiness and permeation characteristic.

The expression "twisted structure" as used herein means a structure where fibers are twisted along the longitudinal direction of the fibers and the frequency of twisting is preferably 2.0/mm or more. The expression "crimped structure" means a structure where fibers are helically crimped along the longitudinal direction of fiber. The expression "folded structure" means a structure where fibers are folded along the longitudinal direction of fiber. The expression "branched structure" means a structure where fibers are branched.

The fiber cross section area and the deviation from circular form of the fiber cross section as described herein are determined by the methods as will be described hereinafter.

The highly bulky cellulose fiber may be made of any material without restriction, so long as the cellulose fiber has the above-mentioned properties. Specific examples thereof include natural cellulose fibers such as pulp and cotton and regenerated cellulose fibers such as rayon and cupranunonium rayon. Either one of these fibers or a mixture thereof may be used. It is preferable to use regenerated cellulose fibers, where the fiber cross section area and cross section form thereof can be arbitrarily controlled, mercerized pulps having a wet-enlarged fiber cross section area and crosslinked pulps having a bulky structure. It is particularly preferable to use a crosslinked pulp, since it can give the bulkiest structure and is available at a low price.

Examples of crosslinking agents for cellulose fibers include N-methylol compounds such as dimethylol ethylene urea and dimethylol dihydroxyethylene urea; polycarboxylic acids such as citric acid, tricarballylic acid and butanetetracarboxylic acid; and polyglycidyl ether compounds. Among these crosslinking agents, polycarboxylic acids and polyglycidyl ether compounds, which evolve no substance toxic to the human body such as formalin, are preferable. Crosslinked pulps obtained with the use of these crosslinking agents can be preferably used as a highly bulky cellulose fiber.

The absorbent paper according to the present invention comprises a surface layer and at least one base layer. Furthermore, it may contain one or more intermediate layers, if necessary. In the production of the absorbent paper of the present invention, the base layers are first sheeted and the surface layer is finally sheeted. It is preferable that a base layer is a layer which has an absorption/diffusion function of powerfully absorbing a liquid and diffusing the same to the whole structure. On the other hand, it is preferable that the surface layer is a layer having a function of quickly absorbing the liquid and allowing smooth penetration of the same toward the base layer.

It is preferable that the base layer has a substantial thickness ranging from 0.2 to 2.0 mm and an absorption height to physiological saline by Klemm's method of from 50 to 150 mm (after 1 minute) and from 100 to 300 mm (after 10 minutes). It is still more preferable that the base layer has a thickness substantially ranging from 0.2 to 1.0 mm and an absorption height to physiological saline by Klemm's method of from 60 to 120 mm (after 1 minute) and from 120 to 250 mm (after 10 minutes).

A base layer having an absorption height by Klemm's method of less than 50 mm (after 1 minute) and 100 mm (after 10 minutes) is not preferred because such a base layer may not be sufficient in the absorption function of the liquid from the surface layer in some cases, whereas a base layer having an absorption height by Klemm's method exceeding 150 mm (after 1 minute) and 300 mm (after 10 minutes) may not be preferred in the case where it is used in combination with a high-absorbent polymer because the flow of the liquid toward the high-absorbent polymer may stagnate in the base layer.

Alternatively, when the substantial thickness of the base layer is less than 0.2 mm, there is a tendency that the amount of the liquid being diffused from the surface layer to the whole structure is reduced. When the substantial thickness exceeds 2.0 mm, a super-thin absorbent paper or absorbent article can be hardly obtained. In this case, there is a tendency that an excessively large space is formed in the step of forming a composite absorbent article composed of the absorbent paper together with a high-absorbent polymer, which makes the smooth migration of the bodily fluid toward the high-absorbent polymer difficult. The basis weight of the base layer may range from 10 to 200 g/m$^2$, preferably from 20 to 200 g/m$^2$.

In the base layer, the inner space structure/space distribution can be controlled over a range from a large space size affecting the initial absorption and diffusion rate to a small space size aiming at enlarging the surface area relating to the diffusion distance by blending the highly bulky cellulose fiber with a hydrophilic microfiber at a definite ratio. Therefore, a base absorption layer which is excellent in the initial absorption rate and the absorption/diffusion capacity (i.e., showing a long diffusion distance) can be easily obtained.

That is to say, it is preferable to produce the base layer by paper-sheeting a material containing from 20 to 80% by weight, on the basis of the total weight of the base layer, of the above-mentioned highly bulky cellulose fiber and from 80 to 20% by weight of the hydrophilic microfiber, namely, a material wherein two or more fibers differing in properties from each other are used. It is still more preferable that the material contains from 30 to 70% by weight of the above-mentioned highly bulky cellulose fiber and from 70 to 30% by weight of the hydrophilic microfiber. When the content of the highly bulky cellulose fiber is less than 20% by weight, an absorbent paper having a sufficient absorption space can be hardly obtained. When it exceeds 80% by weight, on the other hand, the diffusion characteristics tend to be worsened.

Examples of the above-mentioned hydrophilic microfiber include those having hydrophilic fiber surface and a large specific surface area, such as:

(i) fibers having a fiber cross section area of from $0.1 \times 10^{-6}$ cm$^2$ to $2.0 \times 10^{-6}$ cm$^2$ and a deviation from circular form of from 0.1 to 0.5; and (ii) fibers having a specific fiber surface area of from 10 to 20 m$^2$/g. Fibers satisfying either one of the above-mentioned requirements (i) and (ii) are usable without restriction. For example, cellulose fibers such as pulp, cotton and rayon and hydrophilic synthetic fibers such as acrylonitrile and polyvinyl alcohol may be used either alone or in the form of a mixture thereof. A fiber having a fiber cross section area exceeding $2.0 \times 10^{-6}$ cm or a specific fiber surface area of less than 1.0 m$^2$/g has a small surface area and thus the desired diffusion characteristics can hardly be obtained in this case. When the deviation from circular form is 0.5 or above, the microfiber per se hardly undergoes hydrogen bonding and thus the desired diffusion characteristics can scarcely be achieved in this case. On the other hand, a fiber having a fiber cross section area of less than $0.1 \times 10^{-6}$ cm or a specific fiber surface area exceeding 20 m²/g has a too large a surface area and thus there is a tendency that, when used in combination with a high-absorbent polymer, the flow of liquid toward the high-absorbent polymer stagnates in the absorbent paper.

The specific fiber surface area as described herein can be calculated based on the fiber cross section area (W) and the deviation from circular form (O) of the fiber. Alternatively, it can also be determined by known methods such as nitrogen adsorption method, mercury porosimeter method and the like.

In order to stabilize the space structure of the base layer and the whole absorbent paper, a hot-melt adhesive fiber may be added in the step of wet-sheeting, which is preferable since the space structure can be maintained in a stable state even though the absorbent paper is moistened.

Any hot-melt adhesive fibers may be used therefor, so long as they are molten and adhere to each other upon heating. Preferable examples of such a fiber include olefin fibers such as polyethylene, polypropylene, polyester and polyvinyl alcohol fibers; polyethylene/polypropylene composite fiber; polyethylene/polyester composite fiber; low-melting polyester/polyester composite fiber; and fibers having a hydrophilic fiber surface such as polyvinyl alcohol/polypropylene composite fiber and polyvinyl alcohol/polyester composite fiber.

The content of the hot-melt adhesive fiber in the base layer may range from 0 to 30% by weight, preferably from 2 to 20% by weight, on the basis of the total weight of the base layer. When this content exceeds 30% by weight, the absorption/permeation characteristics of the absorbent paper might be deteriorated.

It is preferable that the surface layer has a substantial thickness ranging from 0.2 to 2.0 mm and an absorption height to physiological saline by Klemm's method of 20 to 80 mm (after 1 minute) and 30 to 120 mm (after 10 minutes). It is still preferable that the surface layer has a thickness substantially ranging from 0.2 to 1.0 mm and an absorption height to physiological saline by Klemm's method of 30 to 60 mm (after 1 minute) and 40 to 80 mm (after 10 minutes).

When the substantial thickness is less than 0.2 mm, only an insufficient absorption space for temporarily maintaining the liquid can be obtained. When the substantial thickness exceeds 2.0 mm, on the contrary, the absorption space becomes excessively large and the liquid cannot smoothly migrate toward the base layer. In this case, a super-thin absorbent paper or absorbent article can hardly be obtained. When the absorption height by Klemm's method after 1 minute is less than 20 mm or the absorption height by Klemm's method after 10 minutes is less than 30 mm, the instantaneous absorption rate upon contact of the absorbent paper with the liquid becomes insufficient. When the absorption height by Klemm's method after 1 minute exceeds 80 mm or the absorption height by Klemm's method after 10 minutes exceeds 120 mm, the capacity of the surface layer of absorbing the liquid becomes excessively large. In this case, the liquid cannot smoothly migrate into the base layer but is retained on the surface for a long time after absorption, which deteriorates the re-absorption characteristics and stick-free feel. The basis weight of the surface layer may range from 10 to 200 g/m², preferably from 20 to 100 g/m².

It is preferable that the above-mentioned surface layer is produced by paper-sheeting a material containing a highly bulky cellulose fiber as the main component. In this case, the surface layer consists mainly of a region with a large space size alone. Thus an absorbent surface layer showing an extremely high absorption rate and excellent permeation characteristics can be obtained.

Namely, it is important that the above-mentioned surface layer is produced by paper-sheeting a material which contains from 50 to 98% by weight of a highly bulky cellulose fiber and from 2 to 30% by weight of a hot-melt adhesive fiber, on the basis of the total weight of the surface layer. When the content of the highly bulky cellulose fiber is less than 50% by weight, there is a tendency that the absorption/permeation rate and bulkiness of the surface layer are insufficient for absorbing the liquid. On the contrary, a content of the highly bulky cellulose fiber exceeding 98% by weight makes paper-sheeting difficult. When the content of the hot-melt adhesive fiber is less than 2% by weight, there is a tendency that the binding force, in particular the wet-binding force, becomes insufficient. On the contrary, a content of the hot-melt adhesive fiber exceeding 30% by weight is liable to lower the absorption rate and the permeation rate.

As the highly bulky cellulose fiber, those similar to the ones employed in the base layer may be used without restriction. Similarly, the hot-melt adhesive fibers employed in the base layer may be used in the surface layer without restriction.

In addition to the components as described above, the base layer and surface layer may optionally contain, for example, water-soluble binders and paper-sheeting aids to thereby achieve the optimum toughness, thickness and absorption characteristics of the absorbent paper. Examples of the water-soluble binders include water-soluble resins such as polyvinyl alcohol and sizing agents such as starch. Examples of the paper-sheeting aids include those capable of imparting a sufficient strength to the absorbent paper, e.g., natural pulps such as wood pulp and straw pulp. Examples of further additional components include chemical pulps such as kraft pulp and soda pulp; hydrophilic fibers such as cotton and rayon fibers; and high-absorbent polymers represented by polyacrylates.

The absorbent paper of the present invention may have a two-layer structure wherein a surface layer is directly located on the base layer. Alternately, it may have a three- or more layer structure wherein one or more intermediate layers are located on the base layer and a surface layer is further located thereon.

In the case of the two-layer structure consisting of a base layer and a surface layer, for example, the surface layer produced by paper-sheeting in accordance with the composition range as specified above is laminated on the base layer. For the smooth migration of the absorbed liquid to the base layer without being retained in the surface layer, it is preferable to form the absorbent paper by selecting such a combination that the absorption heights by Klemm's method after 1 and 10 minutes of the base layer are respectively higher than the absorption heights by Klemm's method after 1 and 10 minutes of the surface layer. By constructing such a structure, the liquid would smoothly penetrate from the surface layer to the base layer without being retained on the surface and thus an absorbent having a comfortable stick-free feel can be obtained.

In some cases where, for example, an extremely large amount of a liquid should be absorbed or the absorbent article should be used for a prolonged period of time, the absorbent paper may be provided with one or more intermediate layers to thereby enlarge the absorption space.

The structure of the intermediate layer may be appropriately selected depending on the purpose. For example, an intermediate layer which is produced by paper-sheeting a material containing from 30 to 90% by weight of a highly bulky cellulose fiber, from 10 to 60% by weight of a hydrophilic microfiber and from 0 to 30% by weight of a hot-melt adhesive fiber, each on the basis of the total weight of the intermediate layer, and having a basis weight of from 10 to 100 g/m$^2$, may be preferably employed.

For the smooth migration of the absorbed liquid to the base layer without being retained in the surface layer, it is preferable to control the absorption heights by Klemm's method after 1 and 10 minutes of the intermediate layer respectively to levels higher than the corresponding ones of the surface layer but lower than those of the base layer. The absorption height by Klemm's method of the intermediate layer may be controlled preferably by varying the composition ratio of the above-mentioned highly bulky cellulose fiber to the hydrophilic microfiber. In particular, it is the easiest method therefor to control the content of the hydrophilic microfiber. For example, the hydrophilic microfiber is used in the intermediate layer in a content (% by weight) larger than its content (% by weight) in the surface layer but smaller than its content (% by weight) in the base layer.

In order to obtain a multi-layer absorbent paper by laminating the above-mentioned surface layer and base layers, absorbent papers may be bonded to each other by using an appropriate hydrophilic binder or by a mechanical means such as embossing. It is particularly preferable to obtain an absorbent paper of an integral structure by effecting multi-layer paper-sheeting in the step of wet sheeting and hot-melting the layers to each other with the use of a hot-melt adhesive fiber in the step of drying or by forming hydrogen bonds between a water-soluble binder such as polyvinyl alcohol and pulp. In the absorbent paper obtained by this method, fibers closely interlock together and thus layers do not separate from each other. Thus, the absorbed liquid is not retained among the layers but is smoothly transferred to the base layer, thereby achieving excellent absorption characteristics. According to this method, furthermore, paper-sheeting, compositing and drying of each layer can be carried out in a single step, which is advantageous from the viewpoints of cost and convenience in the process.

The multi-layer paper-sheeting in the wet sheeting step can be performed by a known method by using, for example, a multi-layer paper machine. When a two-layer paper machine comprising a first paper machine and a second paper machine is employed as the multi-layer paper machine, for example, the base layer is sheeted by the first paper machine while the surface layer is paper-sheeted by the second one. After compositing, the obtained composite product is dried with a Yankee drier. Thus an absorbent paper consisting of two layers, i.e., the base layer and the surface layer can be produced. Further, an absorbent consisting of three layers including a base layer, an intermediate layer and a surface layer can be produced by using a multi-layer paper machine comprising a first paper machine, a second paper machine and a third paper machine whereby the base layer, the intermediate layer and the surface layer are paper-sheeted respectively with the first, second and third paper machines, followed by the formation of a composite material and drying with a Yankee drier.

The multi-layer paper sheeting in the wet sheeting step can be performed by another method using, for example, a paper machine comprising one paper machine and plural nozzles for blowing out the paper material onto the paper-making wire. Namely, an absorbent paper consisting of two layers including a base layer and a surface layer can be produced by separately blowing out the materials for the base layer and the surface layer from two nozzles to form respective layers and then paper-sheeting these two layers simultaneously. Similarly, an absorbent paper consisting of three layers including a base layer, an intermediate layer and a surface layer can be produced by separately blowing out the materials for the base layer, the intermediate layer and the surface layer from three nozzles to form respective layers and then paper-sheeting these three layers simultaneously.

In the absorbent paper of the present invention thus obtained, a liquid is quickly absorbed by the surface layer and transferred to the base layer where the liquid migrating from the surface layer is powerfully absorbed and diffused in the whole layer. That is to say, the absorbent paper is designed with the use of layers being excellent in the capability of diffusion and thus an ideal liquid flow (absorption/permeation/diffusion) can be achieved.

Next, the absorbent article according to the present invention wherein the above-mentioned absorbent paper is used will be described in greater detail by reference to the attached drawings.

As FIG. 1 shows, the absorbent article 10 of the present invention has a surface material 1, an absorbent 2 capable of retaining a liquid, and a liquid-impermeable leakproof material 3. The absorbent 2 consists, at least partly, of the above-mentioned absorbent paper 2A and a high-absorbent polymer 2B. This absorbent 2 can be molded into a super-thin form to thereby improve the fitness to the user and provide a longitudinally long shaped absorbent article 10, which is excellent in absorption characteristics and leakproof, and is of an extremely simple constitution.

That is to say, in the absorbent article 10 provided with the above-mentioned absorbent paper 2A and the high-absorbent polymer 2B, the bodily fluid passing through the liquid-permeable surface material 1 can be quickly absorbed by the surface layer of the absorbent paper 2A. Then the bodily fluid is smoothly absorbed and diffused in the back face (the side of the base layer) of the absorbent paper 2A. Subsequently, the bodily fluid, which has been diffused in the absorbent paper, is fixed by the high-absorbent polymer 2B.

Thus the smoother flow of the bodily fluid (absorption/permeation/diffusion/retention) in the absorbent article 10 can be established by locating the surface layer of the absorbent paper 2A adjacent to the liquid-permeable surface material 1, namely, the base layer being in contact with the high-absorbent polymer. It is particularly preferable that the absorbent 2 consists exclusively of a sheet of the absorbent paper 2A and the high-absorbent polymer 2B and the high-absorbent polymer 2B is wound by the absorbent paper 2A. Thus, an absorbent article 10 having a simpler structure and a high performance can be obtained.

The absorbent article 10, in which the absorbent paper 2A according to the present invention is combined with the high-absorbent polymer 2B in an efficient manner, can quickly and surely fix a bodily fluid excreted from the body. Further, neither any liquid residue nor back-flow occurs on the surface material 1 and this absorbent article scarcely suffers from leakage and gives a highly comfortable feel.

The absorbent paper of the present invention, which contains a highly bulky cellulose fiber and comprises two or more layers differing in characteristics from each other, can quickly absorb a fluid in the surface layer and allow the smooth permeation of the liquid to the base layer. In the base layer, on the other hand, the liquid migrating from the surface layer is powerfully absorbed and diffused in the whole layer. Therefore, the absorbent paper of the present invention can establish a highly smooth liquid flow (absorption/permeation/diffusion) without retaining the liquid.

When the absorbent paper of the present invention is used in an absorbent article, the absorbent paper ideally acts on the bodily fluid and smoothly transfers the fluid to the polymer without causing any liquid residue or back-flow to the surface. Thus, the liquid is surely fixed in the polymer. Use of the absorbent paper of the present invention further makes it possible to construct an absorbent, which is superior to conventional ones in the performance, exclusively with a single sheet of the absorbent paper and a polymer. Accordingly, an absorbent article having a very simple structure, a super-thin form, excellent performance of preventing leakage and a highly comfortable feel at use can be thus provided.

To further illustrate the absorbent paper of the present invention and the absorbent articles provided with the same, the following Examples will be given. Although the following Examples relate to sanitary napkins, the present invention is also applicable to paper diapers.

First, absorbent papers of the present invention and comparative ones were produced in the following manner and evaluated in performance.

EXAMPLE 1

As a highly bulky cellulose fiber, 50 parts by weight of a crosslinked pulp having a twisted structure (High Bulk Additive, a product of Weyerhaeuser Paper Company, hereinafter referred to simply as HBA);

as a hydrophilic microfiber, 40 parts of a kraft pulp having a fiber cross section area of $1.9 \times 10^{-6}$ cm$^2$ and a deviation from circular form of the cross section thereof of 0.32 (SKEENA PRIME, a product of Skeena Cellulose, hereinafter referred to simply as NBKP); and as a hot-melt adhesive fiber, 10 parts by weight of polyethylene telephthalate having a thickness of 1.1 denier and a length of 5 mm (TMOTNSB, a product of Teijin Ltd., hereinafter referred to simply as PET), were each dispersed in water and paper-sheeted at a dry basis weight of 50 g/m$^2$ to give a first layer (base layer).

Next, a second layer (surface layer) was paper-sheeted at a dry basis weight of 30 g/m$^2$ by dispersing 90 parts by weight of the above-mentioned HBA and 10 parts by weight of PET in water and laminated on the first layer. After drying, an absorbent paper of a total dry basis weight of 80 g/m$^2$ (Product of the Invention 1) was obtained.

EXAMPLE 2

Sixty parts by weight of the above-mentioned HBA, 35 parts by weight of NBKP and 5 parts of weight of polyvinyl alcohol (Fibribond, a product of Sansho Co., Ltd., hereinafter referred to simply as PVA) employed as a hydrophilic microfiber were each dispersed in water and paper-sheeted at a dry basis weight of 40 g/m$^2$ to give a first layer (base layer).

Next, a second layer (intermediate layer) was paper-sheeted at a dry basis weight of 30 g/m$^2$ by dispersing 70 parts by weight of the above-mentioned HBA, 25 parts by weight of NBKP and 5 parts by weight of PVA in water and laminated on the first layer.

Further, a third layer (surface layer) was paper-sheeted at a dry basis weight of 20 g/m$^2$ by dispersing 95 parts by weight of the above-mentioned HBA and 5 parts by weight of PVA in water and laminated on the second layer. After drying, an absorbent paper of a total dry basis weight of 90 g/m$^2$ (Product of the Invention 2) was obtained.

EXAMPLE 3

As a highly bulky cellulose fiber, 70 parts by weight of a mercerized pulp having a fiber cross section area of $3.8 \times 10^{-6}$ cm$^2$ and a deviation from circular form of the cross section thereof of 0.80 (Porosanier, a product of ITT RAYONIER INC.), 25 parts by weight of NBKP and 5 parts of PET were each dispersed in water and paper-sheeted at a dry basis weight of 60 g/m$^2$ to give a first layer (base layer).

Next, a second layer (surface layer) was paper-sheeted at a dry basis weight of 25 g/m$^2$ by dispersing 70 parts by weight of the above-mentioned HBA, 20 parts by weight of NBKP and 10 parts by weight of PET in water and laminated on the first layer. After drying, an absorbent paper of a total dry basis weight of 85 g/m$^2$ (Product of the Invention 3) was obtained.

EXAMPLE 4

Seventy parts by weight of the mercerized pulp of Example 3 and 30 parts by weight of NBKP were each dispersed in water and paper-sheeted at a dry basis weight of 50 g/m$^2$ to give a first layer (base layer).

Next, a second layer (surface layer) was paper-sheeted at a dry basis weight of 30 g/m$^2$ by dispersing 20 parts by weight of a rayon having a fiber cross section area of $5.9 \times 10^{-6}$ cm$^2$, a deviation from circular form of the cross section thereof of 0.68 and a length of 8 mm (Corona SB Rayon, a product of Daiwabo Rayon Co., Ltd.), 75 parts by weight of the mercerized pulp and 5 parts by weight of PVA in water and laminated on the first layer. After drying, an absorbent paper of a total dry basis weight of 80 g/m$^2$ (Product of the Invention 4) was obtained.

COMPARATIVE EXAMPLE 1

NBKP was dispersed in water and paper-sheeted at a dry basis weight of 50 g/m$^2$ as a first layer (base layer).

Next, a second layer (surface layer) was paper-sheeted at a dry basis weight of 40 g/m$^2$ by dispersing 95 parts by weight of a rayon having a fiber cross section area of $1.3 \times 10^{-6}$ cm$^2$, a deviation from circular form of the cross section thereof of 0.68 and a length of 7 mm (Corona (SB) Rayon, a product of Daiwabo Rayon Co., Ltd.) and 5 parts by weight of PVA in water and laminated on the first layer. After drying, an absorbent paper of a total dry basis weight of 90 g/m$^2$ (Comparative Product 1) was obtained.

COMPARATIVE EXAMPLE 2

NBKP was dispersed in water and paper-sheeted at a dry basis weight of 70 g/m$^2$. After drying, an absorbent paper (Comparative Product 2) was obtained.

COMPARATIVE EXAMPLE 3

Seventy parts by weight of a rayon having a fiber cross section area of $1.3 \times 10^{-6}$ cm$^2$, a deviation from circular form thereof of the cross section of 0.68 and a length of 7 mm and 30 parts by weight of NBKP were dispersed in water and paper-sheeted at a dry basis weight of 70 g/m$^2$. After drying, an absorbent paper (Comparative Product 3) was obtained.

The fiber cross section area and deviation from circular form of the fibers employed in these Examples 1 to 4 and Comparative Examples 1 to 3 were measured by the following methods.

Method for the evaluation of the properties of highly bulky cellulose fiber and hydrophilic microfiber

A. Measurement of fiber cross section area and deviation from circular form:

To measure the fiber cross section area, a fiber was vertically sliced in such a manner as to avoid any change in the cross section area, and a photograph of the cross section of the fiber was taken by means of a electron microscope. Then, fiber cross section was accurately traced with an image analyzer (Avio EXCEL, a product of NIPPON AVIONICS CO., LTD) to thereby measure the fiber cross section area. One hundred fiber cross sections were arbitrarily selected and measured and the average fiber cross section area was calculated.

Based on the photographs of the cross sections, the deviation from circular form of the fiber cross section was subsequently determined with the use of the image analyzer in accordance with the following formula 1. One hundred fiber cross sections were arbitrarily selected and measured and the average deviation from circular form of fiber cross section was determined.

Formula 1:

$$\text{Deviation from circular form } (O) = \frac{4 \times \pi \times (\text{fiber cross section area})}{(\text{peripheral length of fiber cross section})^2}$$

To evaluate the properties of each layer of the absorbent papers of Products of the Invention 1 to 4 obtained in Examples 1 to 4 and Comparative Products 1 to 3 obtained in Comparative Examples 1 to 3, each layer was paper-sheeted separately in the same manner using the same material as in Examples 1 to 4 and Comparative Examples 1 to 3 and then subjected to the following measuring methods. In the paper-sheeting step, the crepe ratio was set to 10%.

Tables 1 to 3 show the results.

Method for measuring properties of absorbent paper

Figure 3:
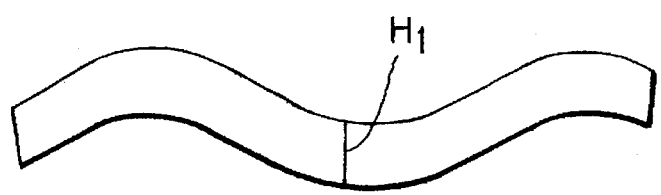
FIG. 3 is a sectional view of an absorbent paper according to the Example.

B. Measurement of substantial thickness:

An absorbent paper was vertically sliced and a photograph of the cross section was taken with a micro-high scope (DIGISCALE 2000, a product of HIROX CO., LTD.). When hairiness made the cross section of the absorbent vague, the boundary was smoothened with an image analyzer (Avio EXCEL, a product of NIPPON AVIONICS CO., LTD.) prior to the measurement. As FIG. 3, which is a model view of the cross section of an absorbent paper shows, the thickness $H_1$ of each absorbent paper layer substantially existing in the cross section was measured. As the measurement points, an arbitrary point on one face of the sample and another point being the closest to the former point on the adjacent face were selected and the distance between these points was measured. Regarding each layer of an absorbent paper sample, measurement was performed at 100 points which were arbitrarily selected and the average was referred to as the substantial thickness.

Figure 4:
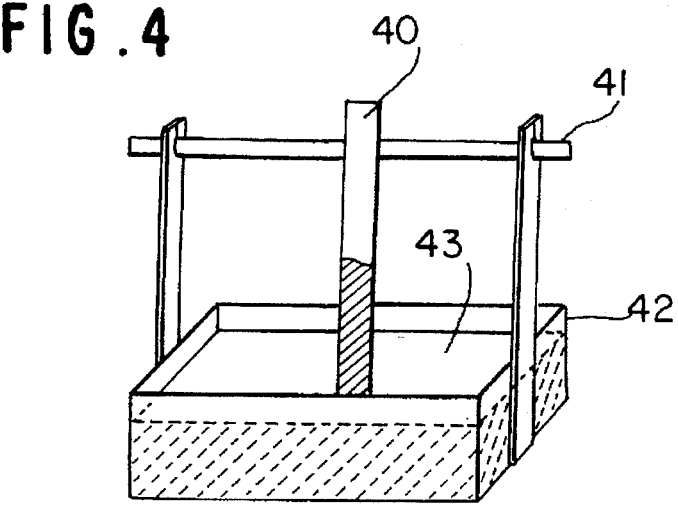
FIG. 4 is a perspective view of an instrument for measuring the absorption height to a liquid by Klemm's method.

C. Measurement of absorption height by Klemm's method after 1 minute and 10 minutes:

An absorbent paper was cut into a piece 40 of 300 mm in length and 20 mm in width. As FIG. 4 shows, this sample piece 40 was hung from a support 41 and tightly fixed at the upper and lower ends. Physiological saline 43 was poured as a test liquid into a rectangular container 42 (300 mm in length×100 mm in width×50 mm in depth) to a depth of 40 mm. Then the sample piece 40 was immersed in the physiological saline 43. One minute and 10 minutes after immersing the sample piece 40, the height (from the liquid surface) of the test solution absorbed by the sample piece 40 was measured. This measurement was repeated by using 10 sample pieces and the average values were referred to as the absorption height by Klemm's method after 1 minute ($h_1$) and the absorption height by Klemm's method after 10 minutes ($h_{10}$) of the physiological saline 43.

TABLE 1

| First layer | Product of the Invention | | | | Comparative product | | |
|---|---|---|---|---|---|---|---|
|  | 1 | 2 | 3 | 4 | 1 | 2 | 3 |
| Composition (part by weight) | | | | | | | |
| High-bulkiness cellulose fiber: | | | | | | | |
| HBA | 50 | 60 | — | — | — | — | — |
| mercerized pulp | — | — | 70 | 70 | — | — | — |
| Corona SB rayon | — | — | — | — | — | — | — |
| Hydrophilic microfiber: | | | | | | | |
| NBKP | 40 | 35 | 25 | 30 | 100 | 100 | 30 |
| Corona (SB) rayon | — | — | — | — | — | — | 70 |
| Hot-melt adhesive fiber: | | | | | | | |
| PET | 10 | — | 5 | — | — | — | — |
| PVA | — | 5 | — | — | — | — | — |
| Properties: | | | | | | | |
| Basis weight (g/m²) | 50 | 40 | 60 | 50 | 50 | 70 | 70 |
| Substantial thickness (mm) | 0.25 | 0.40 | 0.32 | 0.29 | 0.12 | 0.16 | 0.19 |
| Absorption height by Klemm's method (mm): | | | | | | | |
| after 1 min. | 80 | 78 | 68 | 77 | 40 | 45 | 80 |
| after 10 min. | 185 | 175 | 165 | 192 | 92 | 97 | 195 |

TABLE 2

| Second layer | Product of the Invention | | | | Comparative product | | |
| --- | --- | --- | --- | --- | --- | --- | --- |
|  | 1 | 2 | 3 | 4 | 1 | 2 | 3 |
| Composition (part by weight) | | | | | | | |
| High-bulkiness cellulose fiber: | | | | | | | |
| HBA | 90 | 70 | 70 | — | — | — | — |
| Mercerized pulp | — | — | — | 75 | — | — | — |
| Corona SB rayon | — | — | — | 20 | — | — | — |
| Hydrophilic microfiber: | | | | | | | |
| NBKP | — | 25 | 20 | — | — | — | — |
| Corona (SB) rayon | — | — | — | — | 95 | — | — |
| Hot-melt adhesive fiber: | | | | | | | |
| PET | 10 | — | 10 | — | — | — | — |
| PVA | — | 5 | — | 5 | 5 | — | — |
| Properties: | | | | | | | |
| Basis weight (g/m$^2$) | 30 | 30 | 25 | 30 | 40 | — | — |
| Substantial thickness (mm) | 0.25 | 0.21 | 0.23 | 0.21 | 0.22 | — | — |
| Absorption height by Klemm's method (mm) | | | | | | | |
| after 1 min. | 70 | 68 | 65 | 40 | 5 | — | — |
| after 10 min. | 90 | 135 | 98 | 65 | 10 | — | — |

TABLE 3

| Third layer | Product of the Invention | | | | Comparative product | | |
| --- | --- | --- | --- | --- | --- | --- | --- |
|  | 1 | 2 | 3 | 4 | 1 | 2 | 3 |
| Composition (part by weight) | | | | | | | |
| High-bulkiness cellulose fiber: | | | | | | | |
| HBA | — | 95 | — | — | — | — | — |
| Mercerized pulp | — | — | — | — | — | — | — |
| Corona SB rayon | — | — | — | — | — | — | — |
| Hydrophilic microfiber: | | | | | | | |
| NBKP | — | — | — | — | — | — | — |
| Corona (SB) rayon | — | — | — | — | — | — | — |
| Hot-melt adhesive fiber: | | | | | | | |
| PET | — | — | — | — | — | — | — |
| PVA | — | 5 | — | — | — | — | — |
| Properties: | | | | | | | |
| Basis weight (g/m$^2$) | — | 20 | — | — | — | — | — |
| Substantial thickness (mm) | — | 0.20 | — | — | — | — | — |
| Absorption height by Klemm's method (mm) | | | | | | | |
| after 1 min. | — | 58 | — | — | — | — | — |
| after 10 min. | — | 85 | — | — | — | — | — |

Next, the absorbent papers of Products of the Invention 1 to 4 and Comparative Products 1 to 3 were evaluated by the following methods. Table 4 shows the results.

Figure 5:
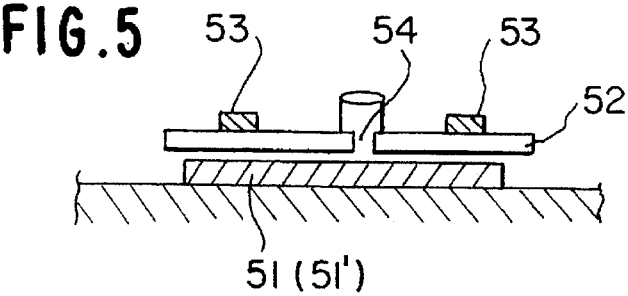
FIG. 5 is a sectional view of an instrument for measuring the liquid absorption time, the liquid-spreading area and the dynamic back-flow of an absorbent paper or an absorbent article.

Method for evaluating absorbent paper a. Measurement of absorption time and liquid-spreading area:

As FIG. 5 shows, an absorbent paper sample 51 (200 mm×75 mm) was horizontally located and an acrylic resin plate 52 provided with an inlet 54 (10 mm in diameter) was placed thereon. Further, weights 53 were placed thereon to thereby apply a force of 5 g/cm$^2$ onto the absorbent paper 51. Then 6 g of artificial blood was poured from the inlet and the time (seconds) required for the complete absorption of the liquid was measured. This measurement was repeated by using 10 samples and the average was referred to as the absorption time (seconds).

Figure 6:
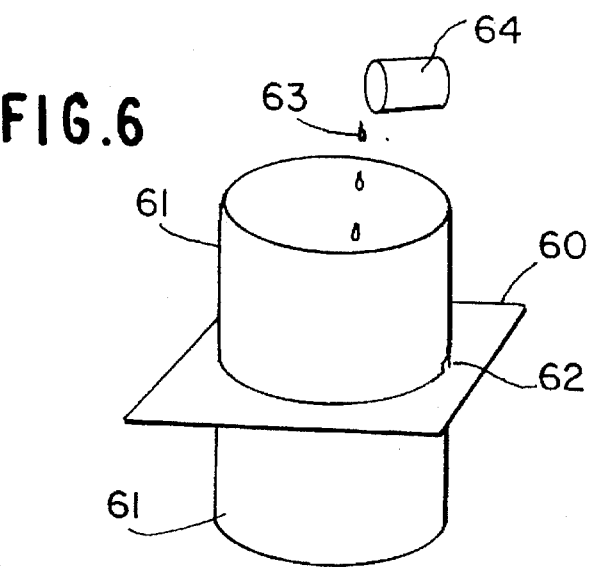
FIG. 6 is a perspective view of an apparatus for measuring the liquid passage time.

After the completion of the absorption of the liquid, the absorbent paper sample was allowed to stand as such for 20 minutes. Then the liquid-spreading area (cm$^2$) was measured by image analysis. This measurement was repeated by using 10 samples and the average values on the face and the back were respectively referred to as the liquid-spreading areas (cm$^2$).

b. Measurement of liquid-passage time:

Liquid-passage time was measured by using an apparatus as shown in FIG. 6.

First, a sample piece 60 of a liquid-passage layer (50 mm in length×50 mm in width) was prepared. Then this sample piece 60 was put between glass tubes 61 (35 mm in inner diameter). Then the sample piece was fixed with the use of clips 62 from both sides via silicone rubber so as to prevent the side-leakage of the liquid during the measurement. As a test liquid, 10 g of a 85% aqueous solution of glycerol of the composition as specified below was weighed into a 10 ml beaker 64 and gently poured into the upper tube. After pouring the 85% aqueous solution of glycerol 63, the time required for the appearance of the surface of the sample piece 60 at a ratio 50% or more to the opening area of the glass tube 61 was determined and referred to as the liquid-passage time.

The test solution was prepared by mixing 85 g of glycerol (a product of Wako Pure Chemical Industries, Ltd.) with 15 of ion-exchanged water and coloring the obtained solution by adding 0.01 g of an edible colorant Blue No. 1 (a product of Tokyo Kasei Kogyo Co., Ltd.)

TABLE 4

| Evaluation | Product of the Invention | | | | Comparative product | | |
| --- | --- | --- | --- | --- | --- | --- | --- |
|  | 1 | 2 | 3 | 4 | 1 | 2 | 3 |
| Absorption time | 25 | 25 | 35 | 48 | 265 | 423 | 83 |
| Liquid-spreading area (cm$^2$) | | | | | | | |
| Face | 72 | 75 | 65 | 68 | 60 | 110 | 152 |
| Back | 135 | 142 | 116 | 145 | 138 | 110 | 152 |
| Liquid-passage time (sec.) | 28 | 25 | 32 | 38 | 175 | 351 | 121 |

Next, the absorbent article 10 (sanitary napkin) of the Example will be described based on FIG. 1. As FIG. 1 shows, the absorbent article 10 of this Example basically consisted of a liquid-permeable surface material 1, a liquid-retaining absorbent 2 and a liquid-impermeable leakproof material 3 and the above-mentioned Products of the Invention (absorbent papers) 1 to 4 were employed at least in the absorbent 2. In the Comparative Examples, the above-mentioned comparative products (absorbent papers) 1 to 3 were used as a substitute for the absorbent paper of the present invention.

In the surface material 1 employed in the following Examples 5 to 8 and Comparative Examples 4 to 6, the surface sheet A or B as specified below was used.

[Surface sheet A]

Figure 2:
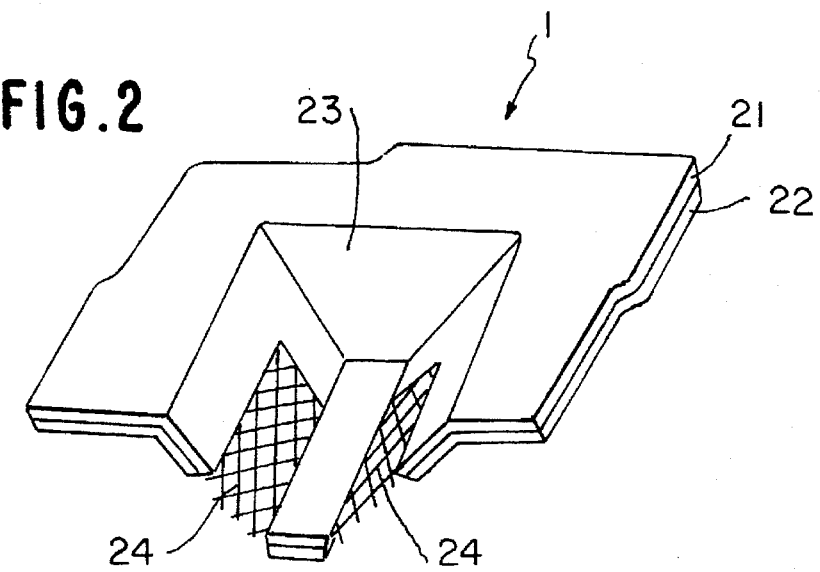
FIG. 2 is a partially cutaway perspective view of a surface sheet A which is employed in the absorbent article of FIG. 1.

As FIG. 2 shows, a low density polyethylene 21 (25 μm, a product of Mitsui Petrochemical Industries, Ltd.) was laminated on a dry heat-bonded nonwoven fabric 22 having a basis weight of 25 g/m$^2$, wherein a polyethylene/ polypropylene composite fiber (a product of Chisso Co.) having 0.34% by weight of a mixed surfactant (alkyl phosphate/sorbitan fatty acid ester) adhering thereto. Thus, a surface sheet provided with pores 24 (0.1 to 2 mm$^2$ in size) at a distribution ratio of 52/cm$^2$ on the wall 23 was obtained. This product was referred to as the surface sheet A.

[Surface sheet B]

The surface sheet (nonwoven fabric) of a marketed sanitary napkin (Lorrie, a product of Kao Corp.) was referred to as the surface sheet B.

EXAMPLE 5

As FIG. 1 shows, the absorbent paper of Product of the Invention 1 (195 mm in length×170 mm in width) was used as the absorbent paper 2A. The absorbent paper 2A had a high-absorbent polymer 2B wound thereby and it was arranged in the manner that the surface layer (second layer) faced to the side of the absorbent face 10A of the absorbent article 10 and the base layer (first layer) faced to the high-absorbent polymer 2B side.

The high-absorbent polymer 2B, which comprised sodium polyacrylate (Polymer Q, a product of Kao Corp.), was almost uniformly dispersed within the area of 70 mm in width and 195 mm in length at a basis weight of 50 g/m$^2$. This material was referred to as the absorbent 2.

This absorbent 2 was wrapped with a leakproof material 3 (polyethylene laminate sheet), further wrapped with a surface material (the above-mentioned surface sheet A) and then fixed with an adhesive 4. The opposite side of the absorption face 10A of the absorbent article 10 was provided with a fixing tape 5 and a peelable paper 6. This product was referred to as Product of the Invention 5.

EXAMPLE 6

An absorbent article was produced in the same manner as the one described in Example 5 but replacing the absorbent paper of Product of the Invention 1 employed in Example 5 by Product of the Invention 2. The obtained absorbent article was referred to as Product of the Invention 6.

EXAMPLE 7

An absorbent article was produced in the same manner as the one described in Example 5 but replacing the absorbent paper of Product of the Invention 1 employed in Example 5 by Product of the Invention 3. The obtained absorbent article was referred to as Product of the Invention 7.

EXAMPLE 8

An absorbent article was produced in the same manner as the one described in Example 5 but replacing the absorbent paper of Product of the Invention 1 employed in Example 5 by Product of the Invention 4. The obtained absorbent article was referred to as Product of the Invention 8.

EXAMPLE 9

An absorbent article was produced in the same manner as the one described in Example 5 but replacing the surface sheet A employed in Example 5 by the surface sheet B. The obtained absorbent article was referred to as Product of the Invention 9.

COMPARATIVE EXAMPLE 4

An absorbent article was produced in the same manner as the one described in Example 5 but replacing the absorbent paper of Product of the Invention 1 employed in Example 5 by Comparative Product 1. The obtained absorbent article was referred to as Comparative Product 4.

COMPARATIVE EXAMPLE 5

An absorbent article was produced in the same manner as the one described in Example 5 but replacing the absorbent paper of Product of the Invention 1 employed in Example 5 by Comparative Product 2. The obtained absorbent article was referred to as Comparative Product 5.

COMPARATIVE EXAMPLE 6

An absorbent article was produced in the same manner as the one described in Example 5 but replacing the absorbent paper of Product of the Invention 1 employed in Example 5 by Comparative Product 3. The obtained absorbent article was referred to as Comparative Product 6.

COMPARATIVE EXAMPLE 7

An absorbent article was produced in the same manner as the one described in Comparative Example 4 but replacing the surface sheet A employed in Comparative Example 4 by the surface sheet B. The obtained absorbent article was referred to as Comparative Product 7.

Next, Products of the Invention 5 to 9 and Comparative Products 4 to 7 were evaluated in performance including absorption time, liquid-spreading area, dynamic back-flow and leakage. Table 5 shows the results.

Method for evaluating absorbent article

Absorption time and liquid-spreading area:

The absorption time and liquid-spreading area were measured by using the same instruments as those employed in "a. Measurement of absorption time and liquid-spreading area" of absorbent paper as shown in FIG. 5, except for replacing the sample piece of the absorbent paper 51 by a sanitary napkin 51' (absorbent article). Also, the artificial blood used as a test liquid was replaced by fiber-free horse blood (a product of Nippon Bio-Test Kenkyusho Co., Ltd.).

Dynamic back-flow:

As FIG. 5 shows, a sanitary napkin 51' (absorbent article), employed as a substitute for the absorbent paper sample 51, was horizontally located and an acrylic resin plate 52 provided with an inlet 54 (10 mm in diameter) was placed thereon. Further, weights 53 were placed thereon to thereby apply a force of 5 g/cm$^2$ onto the sanitary napkin 51'. Then 10 g of the fiber-free horse blood (a product of Nippon Bio-Test Kenkyusho Co., Ltd.) was poured from the inlet. After the completion of the absorption of the liquid, the sample was allowed to stand for 20 minutes.

Next, 10 sheets (75 mm in width×195 mm in length) of an absorbent paper of a basis weight of 30 g/m$^2$ were laminated onto the upper face (being in contact with the skin) of the above-mentioned sanitary napkin. Then the sanitary napkin in this state was fitted to the female waist model 70 of FIG. 7, as shown in FIG. 8. After putting on shorts, this model made to walk at a rate of 100 steps/min (50 m/min.). After walking, the sanitary napkin and the absorbent paper (10 sheets) were taken out and the amount (g) of the fiber-free horse blood absorbed by the absorbent paper was measured as the back-flow. This measurement was repeated by using 10 sanitary napkin samples and the average was referred to as the dynamic back-flow.

Figure 7:
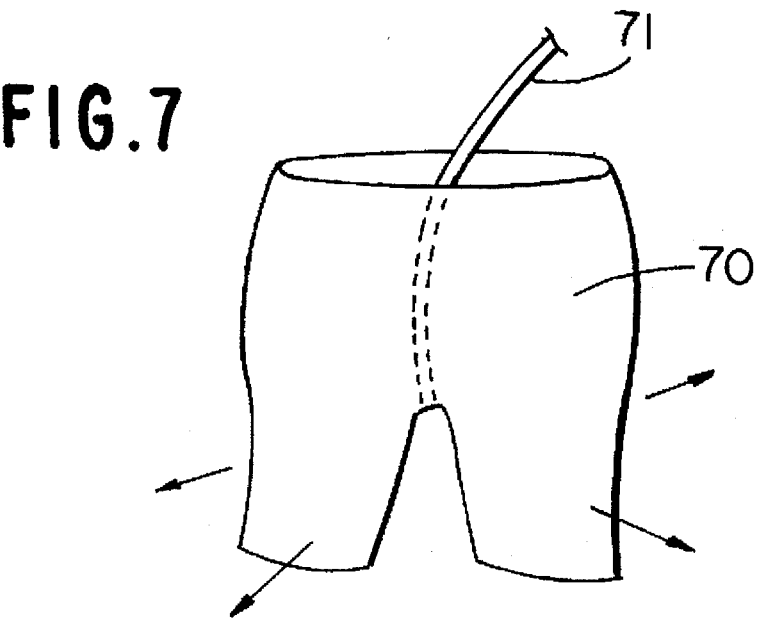
FIG. 7 is a perspective view of a female waist model.
Figure 8:
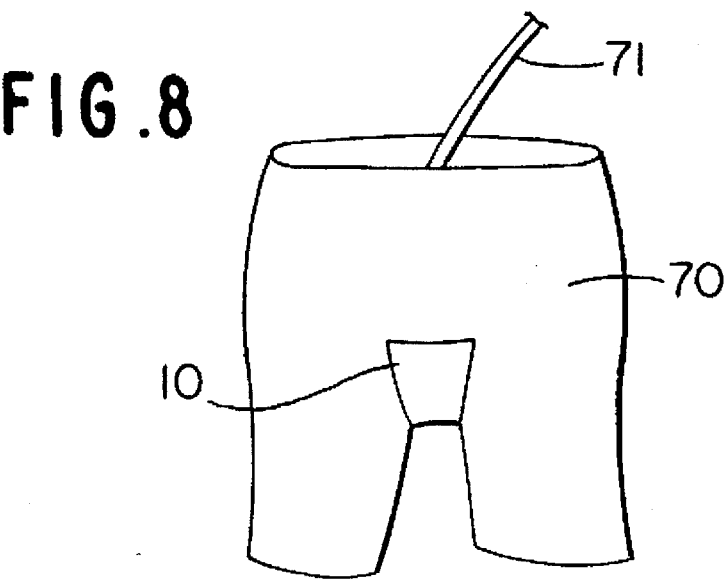
FIG. 8 is a perspective view showing the female waist model to which a sanitary napkin is fitted.

Leakage test:

The obtained sanitary napkin (absorbent article) was fitted to the female waist model 70 of FIG. 7, as shown in FIG. 8. After putting on shorts, this model was made to walk at a rate of 100 steps/minutes (50 m/min.). Next, 3 g of the fiber-free horse blood was introduced into the napkin via a tube 71 while continuously walking the female waist model. The model was made to walk at the same rate for an additional 10 minutes and further 3 g of the fiber-free horse blood was introduced. The same procedure was further repeated. This test was carried out using 10 samples for each sanitary napkin and the number of the napkins suffering from leakage was examined at each time of introduction of the horse blood.

What is claimed is:

1. An absorbent paper comprising a base layer, which is obtained by paper-sheeting a material containing a highly bulky cellulose fiber, and a surface layer being located on said base layer, which is obtained by paper-sheeting a material containing a highly bulky cellulose fiber, wherein said highly bulky cellulose fiber has a fiber cross section area (W) of $3.0 \times 10^{-6}$ cm$^2$ or above.

2. An absorbent paper of claim 1, wherein said highly bulky cellulose fiber is a crosslinked fiber.

3. An absorbent paper of claim 1, wherein said highly bulky cellulose fiber has a deviation from circular form (O) of 0.5 or above.

4. An absorbent paper of claim 1, wherein said surface layer has an absorption height to physiological saline by Klemm's method after 1 minute of from 20 to 80 mm and an absorption height by Klemm's method after 10 minutes of from 30 to 120 mm and said base layer has an absorption height to physiological saline by Klemm's method after 1 minute of 50 mm or above and an absorption height by Klemm's method after 10 minutes of 100 mm or above.

TABLE 5

| Properties and evaluation | Product of the Invention | | | | | Comparative Product | | | |
|---|---|---|---|---|---|---|---|---|---|
| | 5 | 6 | 7 | 8 | 9 | 4 | 5 | 6 | 7 |
| Surface sheet | A | A | A | A | B | A | A | A | B |
| Absorbent paper* | I-1 | I-2 | I-3 | I-4 | I-1 | C-1 | C-2 | C-3 | C-1 |
| Absorption time (sec.) | 15 | 13 | 18 | 20 | 21 | 75 | 112 | 65 | 102 |
| Liquid-spreading area (cm$^2$) | 112 | 115 | 104 | 109 | 117 | 85 | 88 | 113 | 88 |
| Dynamic backflow (g) | 0.1 | 0.1 | 0.2 | 0.3 | 0.3 | 0.8 | 1.2 | 0.6 | 1.1 |
| Leakage number | | | | | | | | | |
| 3 g | 0 | 0 | 0 | 0 | 0 | 0 | 1 | 0 | 1 |
| 6 g | 0 | 0 | 0 | 0 | 0 | 5 | 7 | 3 | 8 |
| 9 g | 0 | 0 | 1 | 2 | 3 | 10 | 10 | 8 | 10 |

Note: Absorbent papers I-1, I-2, I-3 and I-4 respectively mean the absorbent papers of Products of the Invention 1, 2, 3 and 4, while Absorbent papers C-1, C-2 and C-3 respectively mean the absorbent papers of Comparative Products 1, 2 and 3.

The absorbent paper of the present invention has a large absorption space, extremely good absorption/permeation characteristics and extremely good diffusion characteristics. Thus, it is highly excellent in performance. Further, the absorbent paper of the present invention quickly absorbs a liquid, shows a small liquid-spreading area on the surface and causes no retention of the liquid on the surface. Thus, it gives a stick-free, dry feel at use. An absorbent article wherein this absorbent paper is used is a product which has an extremely high absorption capacity, causes little leakage and has a super-thin form. Thus this absorbent article is comfortable for the user.

While the invention has been described in detail and with reference to specific examples thereof, it will be apparent to one skilled in the art that various changes and modifications can be made therein without departing from the spirit and scope thereof.

5. An absorbent paper of claim 4, wherein the absorption heights after 1 and 10 minutes of said base layer are higher respectively than the corresponding ones of the surface layer.

6. An absorbent paper of claim 1, wherein said surface layer is produced by paper-sheeting a material containing from 50 to 98% by weight of a highly bulky cellulose fiber and from 2 to 30% by weight of a hot-melt adhesive fiber and said base layer is produced by paper-sheeting a material containing from 20 to 80% by weight of a highly bulky cellulose fiber and from 80 to 20% by weight of a hydrophilic microfiber.

7. An absorbent paper of claim 1, which is produced by laminating said base layer and said surface layer by multilayer paper-sheeting in a wet-sheeting step.

* * * * *